United States Patent [19]
Hasegawa et al.

[11] Patent Number: 5,731,465
[45] Date of Patent: Mar. 24, 1998

[54] PROCESS FOR THE PREPARATION OF TERTIARY BUTYL HYDRAZINE HYDROHALOGENIDE

[75] Inventors: Yoichi Hasegawa; Mineo Nakagawa; Shunji Hyoda; Hiroyuki Fujita; Takafumi Kawada, all of Sakaide, Japan

[73] Assignee: Japan Hydrazine Co., Ltd., Japan

[21] Appl. No.: 747,002

[22] Filed: Nov. 7, 1996

[30] Foreign Application Priority Data

Dec. 13, 1995 [JP] Japan ................................. 7-324658

[51] Int. Cl.$^6$ ............................................. C07C 241/02
[52] U.S. Cl. ................................................. 564/464
[58] Field of Search ..................................... 564/464

[56] References Cited

U.S. PATENT DOCUMENTS

| | | | |
|---|---|---|---|
| 4,310,696 | 1/1982 | Hojo et al. | 564/464 |
| 4,435,600 | 3/1984 | Hasegawa et al. | 564/464 |
| 4,954,655 | 9/1990 | Kelly | 564/464 |

FOREIGN PATENT DOCUMENTS

| | | | |
|---|---|---|---|
| 1226862 | 9/1989 | Japan | 564/464 |

Primary Examiner—Richard L. Raymond

[57] ABSTRACT

An industrially and economically advantageous process for the preparation of a TBH-HX using starting materials which are cheaply available and are easy to handle, maintaining a high yield. A tertiary butyl hydrazine hydrohalogenide is prepared by reacting a hydrazine hydrohalogenide with a methyl tertiary butyl ether in the presence of an acid.

17 Claims, No Drawings

PROCESS FOR THE PREPARATION OF TERTIARY BUTYL HYDRAZINE HYDROHALOGENIDE

BACKGROUND OF THE INVENTION

1. (Field of the Invention)

A tertiary butyl hydrazine (hereinafter abbreviated as TBH) is a very useful substance as a starting material for producing azine compounds and derivatives thereof.

The present invention is concerned with a novel process for the preparation of TBH. More specifically, the invention is concerned with a process for the preparation of a tertiary butyl hydrazine hydrohalogenide (hereinafter abbreviated as TBH-HX) by reacting a hydrazine hydrohalogenide (hereinafter abbreviated as H-HX) with a methyl tertiary butyl ether (hereinafter abbreviated as MTBE) in the presence of an acid (hereinafter referred to as HA). The invention is further related to a process for the preparation of a TBH by separating, as desired, the TBH from the TBH-HX obtained by the above method.

2. (Description of the Prior Art)

The present inventors have previously invented a process for preparing a TBH from a TBH-HX that is obtained by reacting the H-HX with a tertiary butyl halide (hereinafter abbreviated as t-BuX) (Japanese Patent Publication No. 21267/1982, prior art 1).

The inventors have further invented a process for preparing a TBH-HX by reacting an industrially or economically advantageous tertiary butanol (t-BuOH) with the H-HX (Japanese Patent Publication No. 48823/1986, prior art 2).

Furthermore, Japanese Patent Publication No. 42260/1995 discloses a process for obtaining a TBH by reacting a hydrazine with an isobutylene in the presence of an inorganic acid (prior art 3).

However, the t-BuX used in the prior art 1 is obtained from t-BuOH and HX. To quantitatively react them together, however, it becomes necessary to use concentrated hydrochloric acid in an amount about three times as large as the stoichiometric amount, arousing a troublesome problem of treating waste acid.

The prior art 2 has succeeded in synthesizing the tertiary butyl hydrazine hydrohalogenide directly from the t-BuOH, which is meaningful. The problem, however, remains in that the tertiary butanol is expensive compared to other starting materials for butylation, i.e., compared to the MTBE which is a starting material used in the process of the present invention.

The isobutylene which is a starting material used in the prior art 3 is a gas having a boiling point of −6.9° C., involving a problem in regard to its handling.

SUMMARY OF THE INVENTION

The object of the present invention is to provide an industrially and economically advantageous process for the preparation of a TBH-HX, which is capable of preparing the TBH-HX maintaining a high yield by using starting materials which are cheaper and are easier to handle than those used in the above-mentioned prior arts.

The present inventors have conducted keen study, and have found a process for the preparation of a TBH-HX by reacting an H-HX with an MTBE which is easy to handle and is economically advantageous in the presence of an acid, and have thus arrived at the present invention.

That is, the present invention provides a process for the preparation of a tertiary butyl hydrazine hydrohalogenide (TBH-HX) comprising reacting a hydrazine hydrohalogenide (H-HX) with a methyl tertiary butyl ether (MTBE) in the presence of an acid (HA). A free tertiary butyl hydrazine (TBH) can be easily and efficiently isolated from the obtained TBH-HX by a conventional method that will be described later.

In the present invention, it is desired to use, as an acid, at least the one selected from the group consisting of inorganic acids such as hydrochloric acid, hydrobromic acid, sulfuric acid and phosphoric acid, etc., or the group consisting of organic acids such as p-toluenesulfonic acid, etc.

DETAILED DESCRIPTION OF THE PREFERRED EMBODIMENTS

The preparation process of the present invention is expressed by the following reaction formula (1):

$$H-HX + MTBE \xrightarrow{HA\ (acid)} TBH-HX + CH_3OH \qquad (1)$$

According to the reaction of the present invention as expressed by the above formula (1), a tertiary butyl hydrazine hydrohalogenide is formed from a methyl tertiary butyl ether and a hydrazine hydrohalogenide. Here, in conducting the reaction, the acid works as a catalyst enabling the tertiary butyl hydrazine hydrohalogenide to be formed maintaining a yield of 95% or higher.

Though the mechanism of the reaction has not been clarified yet, it is considered that the tertiary butyl hydrazine hydrohalogenide is formed through the cleavage of the methyl tertiary butyl ether. In this case, a methyl hydrazine hydrohalogenide could have been formed together with the tertiary butyl hydrazine hydrohalogenide. According to the reaction of the present invention, however, the tertiary butyl hydrazine hydrohalogenide is formed very highly selectively, and the methyl hydrazine hydrohalogenide is by-produced very little, which is quite an astonishing fact.

As the hydrazine hydrohalogenide (H-HX) which is a starting material, there can be used a mixture solution of a hydrazine hydrate and an aqueous solution of hydrohalogenic acid such as an aqueous solution of hydrochloric acid or hydrobromic acid, or there can be used a hydrazine hydrohalogenide that has been synthesized in advance.

On the other hand, the methyl tertiary butyl ether (MTBE) is usually the one that is available as an industrial product. Though it is desired that the purity is as high as possible, the methyl tertiary butyl ether may contain by-products or solvent formed in the step of synthesis to a degree that does not impair the reaction of the present invention.

Though the acid (HA) used for the reaction is selected from the group consisting of inorganic acids such as hydrochloric acid, hydrobromic acid, sulfuric acid, phosphoric acid, etc. or the group consisting of organic acids such as p-toluenesulfonic acid, etc., it is particularly desired to use a hydrohalogenic acid such as hydrochloric acid or hydrobromic acid.

In putting the present invention into practice, it is desired that the molar ratio of HA to H-HX, i.e., HA/H-HX, is not larger than 2 and, particularly preferably, from 0.1 to 1.5. It is further desired that the molar ratio of MTBE to H-HX, i.e., MTBE/H-HX, is not larger than 2 and, particularly preferably, from 0.1 to 1.5.

The reaction temperature is usually from 70° to 140° C. and, preferably, from 80° to 130° C. Water can be used as the solvent. It is also allowable to use any other inert solvent so far as it does not impair the reaction. The reaction can be carried out under either a spontaneously produced pressure in a closed system or elevated pressure by, for example, introducing an inert gas.

According to the present invention, the reaction can be conducted according to a variety of operation procedures such as batchwise method or continuous method without any particular limitation. For example, the method may comprise feeding all starting materials substantially at one time at normal temperature, and, then, raising the temperature.

The reaction product according to the present invention contains the desired TBH-HX, methanol, H-HX and HA used in excess amounts, solvent (e.g., water), and small amounts of by-products. After methanol and the solvent (e.g., water, etc.) occupying most of the proportions are distilled off, the reaction product is cooled, and the precipitated TBH-HX which is the object product is isolated.

In this reaction, when the H-HX is used in an excess amount with respect to the MTBE, the unreacted H-HX remains. Conversely, when the MTBE is used in an excess amount with respect to the H-HX, the H-HX remains in a trace amount. In either case, the H-HX and the TBH-HX must be isolated from each other to obtain the TBH-HX of a high purity. For this purpose, the TBH-HX is formed in a saturated manner by using water as a solvent and by recirculating the reaction solution formed as a result of removing by-produced methanol and the like by distillation. Then, the reaction solution or the reaction solution from which methanol and the like are removed, is cooled, so that the TBH-HX of a high purity is precipitated in the form of crystals. Then, the TBH-HX and the H-HX can be isolated from each other by filtration. It is therefore desired that the reaction solution or the reaction solution from which methanol and the like are removed, is recirculated as a mother liquor.

When the reaction temperature is high, the methyl hydrazine hydrohalogenide may be by-produced in small amounts. However, the methyl hydrazine hydrohalogenide is highly soluble in the water and is little crystallized. Besides, when the mother liquor formed as a result of removing the by-produced methanol by distillation is recirculated as a reaction solution, the concentration of the methyl hydrazine hydrohalogenide becomes high, and the reaction for by-producing the methyl hydrazine hydrohalogenide reaches an equilibrium state. Accordingly, the concentration of the methyl hydrazine hydrohalogenide in the mother liquor does not increase beyond a predetermined value (trace amount), and the methyl hydrazine hydrohalogenide is not mixed into the TBH-HX crystals.

According to the process of the present invention as described above, the reaction of the H-HX with the MTBE proceeds very easily making it possible to obtain the TBH-HX of a high purity in high yields.

The obtained TBH-HX can be directly used as a starting material for a variety of synthesis reactions. The TBH of a free form can be obtained as an aqueous solution of TBH by being neutralized with an alkali such as caustic soda followed by distillation. The TBH of a high purity which is substantially anhydrous can be recovered by adding a strong alkali such as caustic soda to the aqueous solution to dehydrate and distill it, or by adding a strong alkali to the aqueous solution to separate the lower aqueous layer and the upper layer of TBH from each other.

EXAMPLES

The invention will now be concretely described by way of Examples to which only, however, the invention is in no way limited.

The tertiary butyl hydrazine hydrochloride and the monomethyl hydrazine hydrochloride were determined by gas chromatography.

(Example 1)

30.04 Grams (0.60 mols) of a 100% hydrazine hydrate, 70.00 g (0.70 mols) of a concentrated hydrochloric acid, 8.80 g (0.10 mols) of a methyl tertiary butyl ether, and 17.54 g of $H_2O$ were fed into a 200-ml pressure-resistant glass bomb, stirred by a shaking machine, and were reacted at 80° C. for one hour.

The reaction solution contained 11.61 g (0.093 mols) of a tertiary butyl hydrazine hydrochloride, yield 93.3%. No monomethyl hydrazine hydrochloride was formed.

(Example 2)

24.98 Grams (0.499 mols) of a 100% hydrazine hydrate, 57.90 g (0.579 mols) of a concentrated hydrochloric acid, and 5.60 g (0.064 mols) of a methyl tertiary butyl ether were fed into the 200-ml pressure-resistant glass bomb, stirred by the shaking machine, and were reacted at 120° C. for one hour.

The reaction solution contained 7.44 g (0.060 mols) of a tertiary butyl hydrazine hydrochloride, yield 94.0%. A monomethyl hydrazine hydrochloride was formed in an amount of 2.12 g (0.026 mols).

(Example 3)

15.45 Grams ( 0.124 mols ) of a tertiary butyl hydrazine hydrochloride, 24.98 g (0.499 mols) of a 100% hydrazine hydrate, 59.20 g (0.592 mols) of a concentrated hydrochloric acid, and 5.50 g (0.062 mols) of a methyl tertiary butyl ether were fed into the 200-ml pressure-resistant glass bomb, stirred by a shaking machine, and were reacted at 80° C. for four hours.

The reaction solution contained 23.21 g (0.186 mols) of a tertiary butyl hydrazine hydrochloride, yield 100%. A monomethyl hydrazine hydrochloride was formed in an amount of 0.14 g (0.002 mols).

A $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 3° C. The amount of white crystals of the obtained tertiary butyl hydrazine hydrochloride was 11.35 g (0.091 mols). No monomethyl hydrazine hydrochloride was contained in the isolated tertiary butyl hydrazine hydrochloride crystals.

(Example 4)

24.92 Grams (0.20 mols) of a tertiary butyl hydrazine hydrochloride, 15.02 g (0.30 mols) of a 100% hydrazine hydrate, 45.00 g (0.45 mols) of a concentrated hydrochloric acid, 8.80 g (0.10 mols) of a methyl tertiary butyl ether, and 17.54 g of $H_2O$ were fed into the 200-ml pressure-resistant glass bomb, stirred by a shaking machine, and were reacted at 100° C. for one hour.

The reaction solution contained 36.50 g (0.293 mols) of a tertiary butyl hydrazine hydrochloride, yield 93.0%. A monomethyl hydrazine hydrochloride was formed in an amount of 0.48 g (0.006 mols).

A $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 1° C. The amount of white crystals of the obtained tertiary butyl hydrazine hydrochloride was 12.52 g (0.10 mols). No monomethyl hydrazine hydrochloride was contained in the isolated tertiary butyl hydrazine hydrochloride crystals.

(Example 5)

24.92 Grams (0.20 mols) of a tertiary butyl hydrazine hydrochloride, 20.02 g (0.40 mols) of a 100% hydrazine hydrate, 55.00 g (0.55 mols) of a concentrated hydrochloric acid, 8.80 g (0.10 mols) of a methyl tertiary butyl ether, and 9.39 g of $H_2O$ were fed into the 200-ml pressure-resistant glass bomb, stirred by a shaking machine, and were reacted at 90° C. for one hour.

The reaction solution contained 36.79 g (0.295 mols) of a tertiary butyl hydrazine hydrochloride, yield 95.4%. A monomethyl hydrazine hydrochloride was formed in an amount of 0.14 g (0.002 mols).

A $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 3° C. The amount of white crystals of the obtained tertiary butyl hydrazine hydrochloride was 17.96 g (0.144 mols). No monomethyl hydrazine hydrochloride was contained in the isolated tertiary butyl hydrazine hydrochloride crystals.

(Example 6)

26.75 Grams (0.215 mols) of a tertiary butyl hydrazine hydrochloride, 10.01 g (0.20 mols) of a 100% hydrazine hydrate, 30.00 g (0.30 mols) of a concentrated hydrochloric acid, 8.80 g (0.10 mol) of a methyl tertiary butyl ether, and 28.88 g of $H_2O$ were fed into the 200-ml pressure-resistant glass bomb, stirred by a shaking machine, and were reacted at 140° C. for one hour.

The reaction solution contained 34.98 g (0.281 mols) of a tertiary butyl hydrazine hydrochloride, yield 65.9%. A monomethyl hydrazine hydrochloride was formed in an amount of 1.86 g (0.023 mols).

(Example 7)

24.92 Grams (0.20 mols) of a tertiary butyl hydrazine hydrochloride, 20.02 g (0.40 mols) of a 100% hydrazine hydrate, 55.00 g (0.55 mols) of a concentrated hydrochloric acid, 8.80 g (0.10 mols) of a methyl tertiary butyl ether, and 9.39 g of $H_2O$ were fed into the 200-ml pressure-resistant glass bomb, stirred by a shaking machine, and were reacted at 140° C. for 30 minutes.

The reaction solution contained 35.31 g (0.283 mols) of a tertiary butyl hydrazine hydrochloride, yield 83.5%. A monomethyl hydrazine hydrochloride was formed in an amount of 0.10 g (0.001 mols).

(Example 8)

149.50 Grams (1.20 mols) of a tertiary butyl hydrazine hydrochloride, 60.07 g (1.20 mols) of a 100% hydrazine hydrate, 180.00 g (1.80 mols) of a concentrated hydrochloric acid, 52.90 g (0.60 mols) of a methyl tertiary butyl ether, and 173.38 g of $H_2O$ were fed into a 1-liter glass autoclave, and were reacted at 100° C. for two hours. A maximum pressure during the reaction was 2.9 kg/cm².

The reaction solution contained 211.52 g (1.697 mols) of a tertiary butyl hydrazine hydrochloride, yield 82.8%. A monomethyl hydrazine hydrochloride was formed in an amount of 2.17 g (0.026 mols).

A $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 25° C. The amount of white crystals of the obtained tertiary butyl hydrazine hydrochloride was 46.14 g (0.360 mols), crystal yield 60.0% , content 97.23%, m.p. 193° C. No monomethyl hydrazine hydrochloride was contained in the isolated tertiary butyl hydrazine hydrochloride crystals.

(Example 9)

149.50 Grams (1.20 mols) of a tertiary butyl hydrazine hydrochloride, 60.07 g (1.20 mols) of a 100% hydrazine hydrate, 180.00 g (1.80 mols) of a concentrated hydrochloric acid, 52.90 g (0.60 mols) of a methyl tertiary butyl ether, and 173.38 g of $H_2O$ were fed into the 1-liter glass autoclave, and were reacted at 100° C. for one hour. A maximum pressure during the reaction was 2.7 kg/cm².

The reaction solution contained 211.25 g (1.695 mols) of a tertiary butyl hydrazine hydrochloride, yield 82.5%. A monomethyl hydrazine hydrochloride was formed in an amount of 0.75 g (0.009 mols).

A $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 16° C. The amount of white crystals of the obtained tertiary butyl hydrazine hydrochloride was 51.56 g (0.396 mols), crystal yield 66.0%, content 95.82%, m.p. 191° C. No monomethyl hydrazine hydrochloride was contained in the isolated tertiary butyl hydrazine hydrochloride crystals.

(Example 10)

11.40 Grams (0.091 mols) of a tertiary butyl hydrazine hydrochloride, 26.23 g (0.524 mols) of a 100% hydrazine hydrate, 61.60 g (0.616 mols) of a concentrated hydrochloric acid, and 45.71 g (0.519 mols) of a methyl tertiary butyl ether were added to 401.30 g of the mother liquor of Example 9 from which the tertiary butyl hydrazine hydrochloride crystals are to be isolated [composition: 117.82 g (0.945 mols) of a tertiary butyl hydrazine hydrochloride, 25.68 g (0.513 mols) of a 100% hydrazine hydrate, 93.90 g (0.939 mols) of a concentrated hydrochloric acid, 1.57 g (0.019 mols) of a monomethyl hydrazine hydrochloride, 2.61 g (0.081 mols) of a $CH_3OH$, 159.75 g of $H_2O$], and were fed into the 1-liter glass autoclave, and were reacted at 100 Åé for one hour. A maximum pressure during the reaction was 3.1 kg/cm².

The reaction solution contained 181.91 g (1.460 mols) of a tertiary butyl hydrazine hydrochloride, yield 81.5%. A monomethyl hydrazine hydrochloride was formed in an amount of 2.33 g (0.028 mols).

The $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 24° C. The amount of white crystals of the obtained tertiary butyl hydrazine hydrochloride was 54.91 g (0.435 mols), crystal yield 83.8% , content 98.73%, m.p. 192° C. No monomethyl hydrazine hydrochloride was contained in the isolated tertiary butyl hydrazine hydrochloride crystals.

(Example 11)

8.60 Grams (0.069 mols) of a tertiary butyl hydrazine hydrochloride, 20.72 g (0.414 mols) of a 100% hydrazine hydrate, 48.50 g (0.485 mols) of a concentrated hydrochloric acid, and 38.61 g (0.438 mols) of a methyl tertiary butyl ether were added to 339.30 g of the mother liquor of Example 10 from which the tertiary butyl hydrazine hydrochloride crystals are to be isolated [composition: 100.70 g (0.808 mols) of a tertiary butyl hydrazine hydrochloride, 18.37 g (0.367 mols) of a 100% hydrazine hydrate, 73.40 g (0.734 mols) of a concentrated hydrochloric acid, 2.95 g (0.036 mols) of a monomethyl hydrazine hydrochloride, 1.36 g (0.042 mols) of a $CH_3OH$, 135.97 g of H2O], and were fed into the 1-liter glass autoclave, and were reacted at 100° C. for one hour. A maximum pressure during the reaction was 2.5 kg/cm².

The reaction solution contained 157.44 g (1.263 mols) of a tertiary butyl hydrazine hydrochloride, yield 88.2%. A monomethyl hydrazine hydrochloride was formed in an amount of 3.08 g (0.037 mols).

The $CH_3OH$ and $H_2O$ in the reaction solution were distilled off, the reaction solution was condensed as a distillation can residue, the tertiary butyl hydrazine hydrochloride was crystallized from the distillation can residue, and the thus formed crystals were isolated at 25° C. The amount of white crystals of the obtained tertiary butyl hydrazine hydrochloride was 43.95 g (0.344 mols), crystal yield 78.5%, content 97.40%, m.p. 190° C. No monomethyl hydrazine hydrochloride was contained in the isolated tertiary butyl hydrazine hydrochloride crystals.

(Example 12)

30.04 Grams (0.60 mols) of a 100% hydrazine hydrate, 60.00 g (0.60 mols) of a concentrated hydrochloric acid, 9.81 g (0.10 mols) of a concentrated sulfuric acid, 8.80 g (0.10 mols) of a methyl tertiary butyl ether, and 6.49 g of $H_2O$ were fed into the 200-ml pressure-resistant glass bomb, stirred by a shaking machine, and were reacted at 90° C. for one hour.

The reaction solution contained 9.74 g (0.078 mols) of a tertiary butyl hydrazine hydrochloride, yield 78.2%. A monomethyl hydrazine hydrochloride was formed in an amount of 0.11 g (0.0013 mols).

(Example 13)

30.04 Grams (0.60 mols) of a 100% hydrazine hydrate, 60.00 g (0.60 mols) of a concentrated hydrochloric acid, 11.53 g (0.10 mol) of a 85% phosphoric acid, 8.80 g (0.10 mol) of a methyl tertiary butyl ether, and 6.49 g of $H_2O$ were fed into the 200-ml pressure-resistant glass bomb, stirred by a shaking machine, and were reacted at 100° C. for one hour.

The reaction solution contained 11.97 g (0.096 mols) of a tertiary butyl hydrazine hydrochloride, yield 96.0%. A monomethyl hydrazine hydrochloride was formed in an amount of 0.06 g (0.0007 mols).

(Example 14)

30.04 Grams (0.60 mols) of a 100% hydrazine hydrate, 20.50 g (0.70 mols) of a 47% hydrobromic acid, 8.80 g (0.10 mol) of a methyl tertiary butyl ether, and 6.49 g of $H_2O$ were fed into the 200-ml pressure-resistant glass bomb, stirred by a shaking machine, and were reacted at 80° C. for one hour.

The reaction solution contained 16.28 g (0.096 mols) of a tertiary butyl hydrazine hydrobromate, yield 96.3%. A monomethyl hydrazine hydrobromate was formed in an amount of 0.37 g (0.0045 mols).

(Example 15)

53.53 Grams (0.430 mols) of a tertiary butyl hydrazine hydrochloride, 20.02 g (0.40 mols) of a 100% hydrazine hydrate, 60.00 g (0.60 mols) of a concentrated hydrochloric acid, 8.29 g (0.101 mols) of a monomethyl hydrazine hydrochloride, 17.64 g (0.20 mols) of a methyl tertiary butyl ether, and 57.80 g of $H_2O$ were fed into a 500-ml pressure-resistant glass bomb, stirred by a shaking machine, and were reacted at 100° C. for 40 minutes.

The reaction solution contained 75.32 g (0.604 mols) of a tertiary butyl hydrazine hydrochloride, yield 87.2%. The amount of the monomethyl hydrazine hydrochloride after the reaction was 6.73 g (0.082 mols). This amount was smaller than the amount of when the reaction was started, indicating that the reaction for by-producing the monomethyl hydrazine hydrochloride was approaching an equilibrium state.

No monomethyl hydrazine hydrochloride was contained in the tertiary butyl hydrazine hydrochloride crystals that were obtained by cooling and isolation.

(Example 16)

30.04 Grams (0.60 mols) of a 100% hydrazine hydrate, 60.00 g (0.60 mols) of a concentrated hydrochloric acid, 19.02 g (0.10 mols) of a hydrate of p-toluenesulfonic acid, 8.80 g (0.10 mols) of a methyl tertiary butyl ether, and 116.40 g of $H_2O$ were fed into the 200-ml pressure-resistant glass bomb, stirred by a shaking machine, and were reacted at 100° C. for one hour.

The reaction solution contained 11.44 g (0.092 mols) of a tertiary butyl hydrazine hydrochloride, yield 91.8%. A monomethyl hydrazine hydrochloride was formed in an amount of 0.16 g (0.0019 mols).

According to the present invention, a tertiary butyl hydrazine hydrohalogenide of a high purity is prepared maintaining a high yield and a high selectivity by reacting a hydrazine hydrohalogenide with a methyl tertiary butyl ether which is cheap and is easy to handle in the presence of an acid.

We claim:

1. A process for the preparation of a tertiary butyl hydrazine hydrohalogenide comprising reacting a hydrazine hydrohalogenide with a methyl tertiary butyl ether in the presence of an acid.

2. A process according to claim 1, wherein the hydrazine hydrohalogenide is obtained by mixing a hydrated hydrazine and a hydrohalogenic acid together.

3. A process according to claim 1, wherein the acid is at least the one selected from the group consisting of hydrohalogenic acid, sulfuric acid, phosphoric acid and p-toluenesulfonic acid.

4. A process according to claim 2, wherein the acid is at least the one selected from the group consisting of hydrohalogenic acid, sulfuric acid, phosphoric acid and p-toluenesulfonic acid.

5. A process according to claim 1, wherein the hydrohalogenide is at least the one selected from the group consisting of hydrochloride and hydrobromate.

6. A process according to claim 2, wherein the hydrohalogenide is at least the one selected from the group consisting of hydrochloride and hydrobromate.

7. A process according to claim 1, wherein the molar ratio of the acid to the hydrazine hydrohalogenide (HA/H-HX) is not larger than 2.

8. A process according to claim 2, wherein the molar ratio of the acid to the hydrazine hydrohalogenide (HA/H-HX) is not larger than 2.

9. A process according to claim 1, wherein the molar ration of the methyl tertiary butyl ether to the hydrazine hydrohalogenide (MTBE/H-HX) is not larger than 2.

10. A process according to claim 2, wherein the molar ration of the methyl tertiary butyl ether to the hydrazine hydrohalogenide (MTBE/H-HX) is not larger than 2.

11. A process according to claim 1, wherein the reaction is carried out at a temperature of from 70° to 140° C.

12. A process according to claim 2, wherein the reaction is carried out at a temperature of from 70° to 140° C.

13. A process according to claim 1, wherein the reaction is carried out in an aqueous medium.

14. A process according to claim 2, wherein the reaction is carried out in an aqueous medium.

15. A process according to claim 1, wherein methanol and water are distilled off from the reaction mixture, the reaction mixture is condensed, the hydrazine hydrohalogenide is crystallized from the obtained condensate, and the hydrazine halogenide is obtained in the form of crystals.

16. A process according to claim 2, wherein methanol and water are distilled off from the reaction mixture, the reaction mixture is condensed, the hydrazine hydrohalogenide is crystallized from the obtained condensate, and the hydrazine halogenide is obtained in the form of crystals.

17. A process for the preparation of a tertiary butyl hydrazine comprising reacting a hydrazine hydrohalogenide with a methyl tertiary butyl ether in the presence of an acid to obtain a tertiary butyl hydrazine hydrohalogenide, neutralizing the obtained tertiary butyl hydrazine hydrohalogenide with an alkali, and distilling the neutralized product to recover a free tertiary butyl hydrazine.

* * * * *